US006888640B2

(12) United States Patent
Spina et al.

(10) Patent No.: US 6,888,640 B2
(45) Date of Patent: May 3, 2005

(54) BODY SPATIAL DIMENSION MAPPER

(76) Inventors: Mario J. Spina, 310 Cabin Rd. SE., Vienna, VA (US) 22180; Anthony M. Desiderio, 205 Holmard St., Gaithersburg, MD (US) 20878

( * ) Notice: Subject to any disclaimer, the term of this patent is extended or adjusted under 35 U.S.C. 154(b) by 449 days.

(21) Appl. No.: 09/738,505

(22) Filed: Dec. 18, 2000

(65) Prior Publication Data

US 2001/0030754 A1 Oct. 18, 2001

Related U.S. Application Data

(60) Provisional application No. 60/180,339, filed on Feb. 4, 2000.

(51) Int. Cl.$^7$ .............................................. G01B 11/24
(52) U.S. Cl. ......................................................... 356/601
(58) Field of Search ................................. 356/601–613; 250/559.22

(56) References Cited

U.S. PATENT DOCUMENTS

| | | | |
|---|---|---|---|
| 4,158,507 A | 6/1979 | Himmel ....................... 356/376 |
| 4,192,613 A | 3/1980 | Hammar ...................... 356/386 |
| 4,343,553 A | 8/1982 | Nakagawa et al. .......... 356/376 |
| 4,349,277 A | 9/1982 | Mundy et al. ............... 356/376 |
| 4,373,804 A | 2/1983 | Pryor et al. ................. 356/376 |
| 4,406,544 A | * 9/1983 | Takada et al. ............... 356/612 |
| 4,529,316 A | 7/1985 | DiMatteo .................... 356/376 |
| 4,634,879 A | 1/1987 | Penney ....................... 356/376 |
| 4,657,394 A | 4/1987 | Halioua ...................... 356/376 |
| 4,721,388 A | 1/1988 | Takagi ........................ 356/376 |
| 4,758,093 A | 7/1988 | Stern .......................... 356/376 |
| 4,790,660 A | 12/1988 | Ito et al. ..................... 356/376 |
| 4,794,262 A | 12/1988 | Sato et al. ............. 250/559.22 |
| 4,874,955 A | 10/1989 | Uesugi et al. .............. 250/550 |
| 4,935,810 A | 6/1990 | Nonami et al. ............... 348/45 |
| 4,939,379 A | 7/1990 | Horn .......................... 250/560 |
| 4,995,716 A | 2/1991 | Warnicki et al. ............ 351/212 |
| 5,102,223 A | 4/1992 | Uesugi et al. .............. 356/376 |
| 5,109,276 A | 4/1992 | Nudelman et al. ............ 348/47 |
| 5,175,595 A | 12/1992 | Fukase ........................ 356/387 |
| 5,177,556 A | * 1/1993 | Rioux ......................... 356/602 |
| 5,530,652 A | * 6/1996 | Croyle et al. ............... 700/130 |
| RE35,816 E | 6/1998 | Schulz ........................ 356/376 |
| 5,771,310 A | 6/1998 | Vannah ....................... 384/154 |
| 5,784,098 A | 7/1998 | Shoji et al. ................... 348/45 |
| 5,850,290 A | * 12/1998 | Horiguchi et al. .......... 356/602 |
| 5,953,448 A | 9/1999 | Liang ......................... 382/159 |
| 6,102,861 A | 8/2000 | Avila et al. ................. 600/493 |
| 6,151,118 A | 11/2000 | Norita et al. ............... 356/376 |

* cited by examiner

*Primary Examiner*—Richard A. Rosenberger

(57) ABSTRACT

A Body Spatial Dimension Mapper (BSDM) comprising a body mapping booth (10), an array of laser range detectors mounted on the top (17) and bottom (18) of the booth, a moveable circular sensor ring (11), a sensor controller and processing unit (13), and a media production unit (14). The BSDM provides a highly automated and accurate method for determining 3-D surface measurements of a human body, a digital representation of the body shape, contour, length, width, and volume measurements, and a digital format of these measurements for storage, transmission, and computer processing. It is applicable to the garment, online clothing retail, and medical industries.

1 Claim, 2 Drawing Sheets

Body Spacial Dimension Mapper (BSDM)

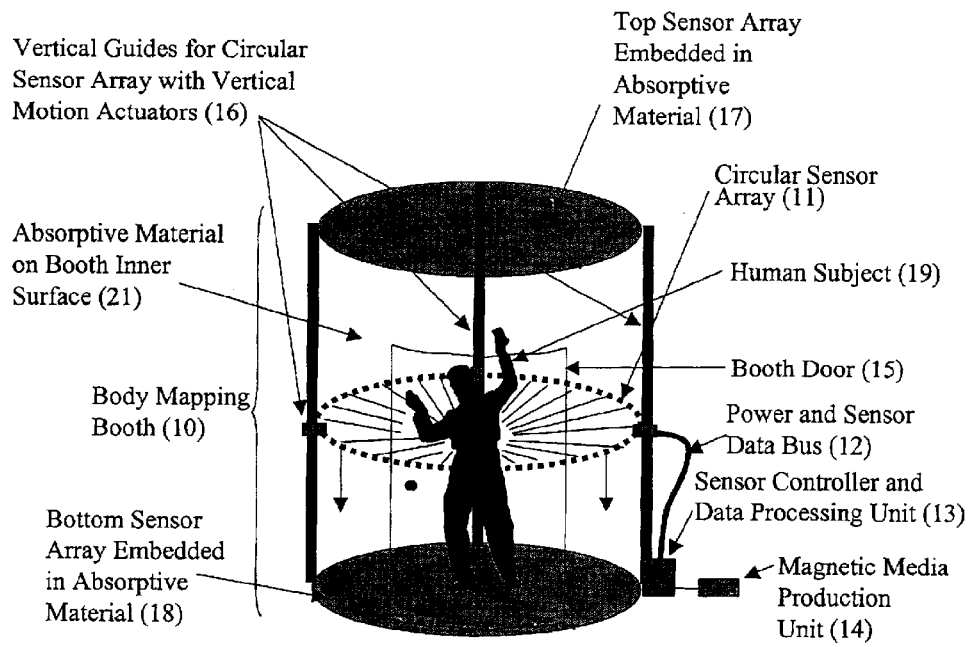
Figure 1. Body Spacial Dimension Mapper (BSDM)
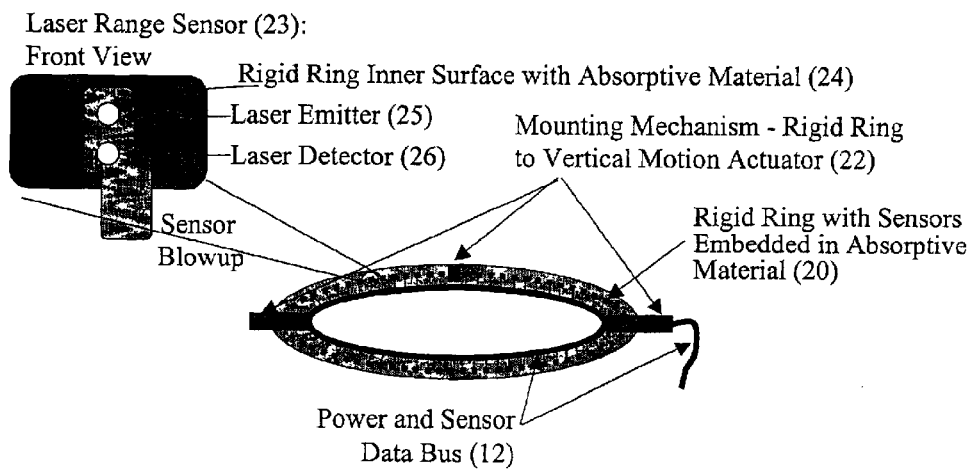
Figure 2. Circular Sensor Array Assembly (11)

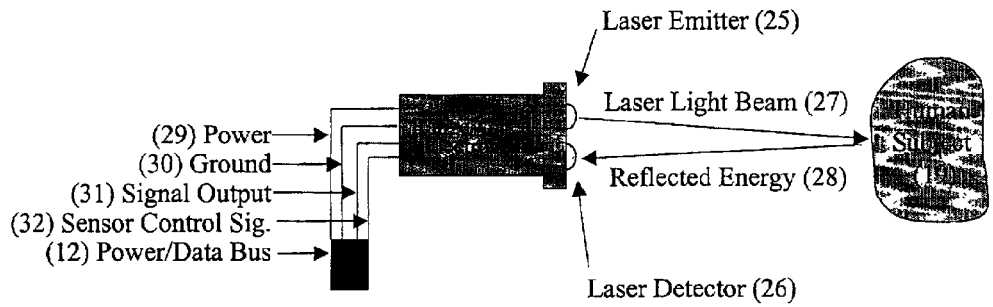
Figure 3. Laser Range Sensor (23): Side View
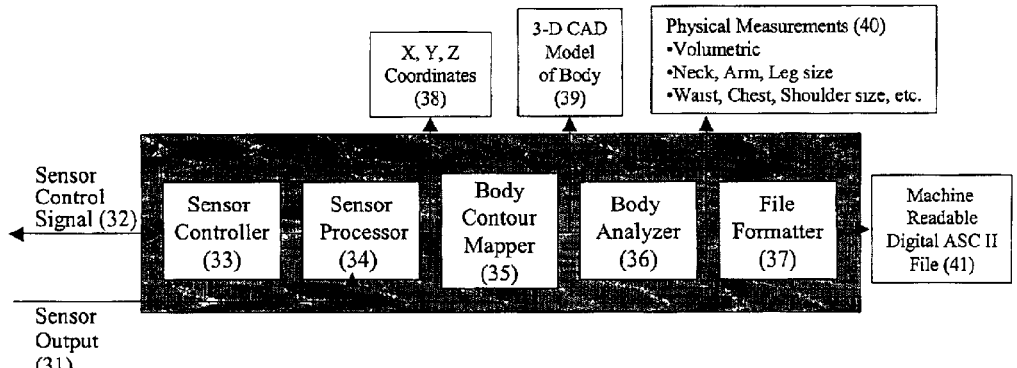
Figure 4. Sensor Controller and Processing Unit (13)
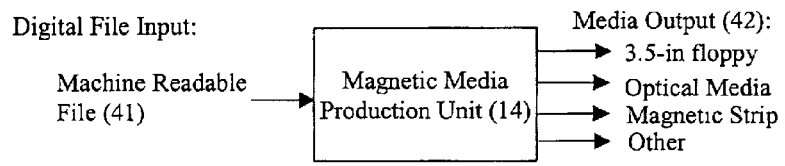
Figure 5. Magnetic Media Production Unit (14)

BODY SPATIAL DIMENSION MAPPER

This application claims the benefit of Provisional Application No. 60/180,339, filed Feb. 4, 2000.

BACKGROUND—FIELD OF INVENTION

This field relates to the art of automatically measuring the dimensions of the human body as applied in the garment and medical industries.

BACKGROUND—DESCRIPTION OF PRIOR ART

Today and in the past, tailors and garment makers have measured the human body dimensions, for the purposes of garment sizing, using a manual process employing rulers and measuring tapes. This well known procedure yields point measurements of the body and not a full three-dimensional (3-D) characterization of body contours and volumetrics.

A survey of prior patents in this field was conducted and patents were found to clearly address the problems of automatically measuring the 3-D surface contours of the entire human body and rendering such information in a digital format for digital transmission and computer processing. The Body Spatial Dimension Mapper (BSDM) provides an apparatus and methodology for scanning the body's surface using an enclosed booth structure with an array of optical ranging sensors. The BSDM's control and processing system provides the algorithms to control sensor position and sampling and for converting sensor position and measurements into a 3-D digital representation of the body. Processing is also provided to produce typical garment industry and medical volumetric measurements (e.g., waist size, inseam length, arm length, and arm, leg, and torso volumes, etc.). The digital file that is produced can be digitally stored, transmitted, or process by a standard computer.

A number of patents have been granted that address the art of 3-D object contour measurement (i.e., U.S. Pat. No. 4,158,507 (1979), U.S. Pat. No. 4,192,316 (1980), U.S. Pat. No. 4,343,553 (1982), U.S. Pat. No. 4,349,277 (1982), U.S. Pat. No. 4,373,804 (1983), U.S. Pat. No. 4,529,316 (1985), U.S. Pat. No. 4,634,879 (1987), U.S. Pat. No. 4,657,394 (1987), U.S. Pat. No. 4,721,388 (1988), U.S. Pat. No. 4,758,093 (1988), U.S. Pat. No. 4,790,660 (1988), U.S. Pat. No. 4,794,262 (1988), U.S. Pat. No. 4,874,955 (1989), U.S. Pat. No. 4,935,810 (1990), U.S. Pat. No. 4,939,379 (1990), U.S. Pat. No. 4,995,716, (1991), U.S. Pat. No. 5,102,223 (1992), U.S. Pat. No. 5,109,276 (1992), U.S. Pat. No. 5,175,595 (1992), RE25816 (1998), U.S. Pat. No. 5,771,310 (1998), U.S. Pat. No. 5,784,098 (1998), U.S. Pat. No. 5,935,448 (1999), U.S. Pat. No. 6,102,861 (2000), U.S. Pat. No. 6,151,118 (2000)). Unlike the BSDM claimed herein, these patents do not, however, provide an apparatus and method for automatically producing a 3-D representation of the entire surface of the human body and for producing a data set for digital storage, transmission, and computer processing.

One patent, given to Liang U.S. Pat. No. 5,935,448 (1999), does specify a methodology for measuring the 3-D surface contours of the human body. Liang employs a photographic apparatus that uses charged coupled devices (CCDs) and a radiated point light source to measure the 3-D coordinates of points on the body's surface by mathematical comparison and triangulation between separated cameras. The BSDM claimed herein uses an optical laser range detection method that requires considerably less algorithmic computation. Further, Liang does not claim an apparatus sufficient to adequately measure the entire surface of the human body.

OBJECTS AND ADVANTAGES

The following are advantages of this invention:

(a) Provides a highly automatic method for determining body shape and contour;

(b) Provides highly accurate measurements of body shape and contour;

(c) Provides a rapid means of dimensioning the human body;

(d) Facilitates a digital representation of the shape, contour, length, width, and volume measurements of the human body;

(e) Provides a digital format for storing human body shape and contour measurements on digital or magnetic memory media;

(f) Provides a digital format for transmitting human body shape, contour, and spatial dimensions of electronic communication systems.

DRAWINGS AND FIGURES

FIG. 1 shows the primary components of the Body Spatial Dimension Mapper to include the body booth enclosure with laser range detectors mounted to the top, bottom, and a movable circular sensor ring and the Sensor Control Processing and Media Production Units.

FIG. 2 shows the movable circular sensor array assembly having fixed mounted laser range detection units.

FIG. 3 provides illustration of the operation of commercially available laser range detection devices for specific point range detection.

FIG. 4 identifies the primary modules composing the Sensor Controller and Processing Unit with indications of inputs and outputs.

FIG. 5 illustrates the input/output operation of the magnetic Media Production Unit.

LIST OF REFERENCE NUMERALS

10—Body Mapping Booth
11—Circular Sensor Array
12—Power and Sensor Data Bus
13—Sensor Controller and Processing Unit (SCPU)
14—Media Production Unit (MPU)
15—Booth Door
16—Vertical Guides for Circular Sensor Array with Vertical Motion Actuators
17—Top Sensor Array Embedded in Absorptive Material
18—Bottom Sensor Array Embedded in Absorptive Material
19—Human Subject
20—Rigid Ring with Sensors Embedded in Absorptive Materials
21—Absorptive Material on Booth Inner Surface
22—Mounting Mechanism—Rigid Ring to Vertical Motion Actuator
23—Laser Range Sensor
24—Rigid Ring Inner Surface with Absorptive Material
25—Laser Emitter
26—Laser Detector
27—Laser Light Beam
28—Reflected Energy 29—Power
30—Ground
31—Signal Output
32—Sensor Control Signal
33—Sensor Controller
34—Sensor Processor
35—Body Contour Mapper
36—Body Analyzer
37—File Formatter
38—Spatial (x, y, z) Coordinates
39—3-D CAD Model
40—Physical Measurements
41—Machine Readable File
42—Media Output

SUMMARY OF THE INVENTION

In accordance with the present invention, an array of range detection devices are mounted to both the moveable and stationary surfaces of a structure that is built to enclose a body for which the three-dimensional coordinates of points along the surface contours of the body are to be measured.

DESCRIPTION OF INVENTION—MAIN EMBODIMENT

The Body Spatial Dimension Mapper (BSDM) is composed of four (4) primary components as shown in FIG. 1. The first is a body booth 10, either circular or rectangular, to surround a human or other body subject to be mapped. The second is an array of laser range sensors, circular 11, top 17, and bottom 18, for making three-dimensional spatial measurements of points on the surface of an enclosed body. The third is a Sensor Control and Processing Unit (SCPU) 13. The power and sensor data bus 12 transmits sensor data to and carries sensor control and positioning signals from the SCPU. The SCPU derives three-dimensional body surface coordinates from sensor measurements and formats the data for machine-readable digital transmission or storage. The fourth is a media production unit (MPU) 14.

The body booth is a dimensionally known, fixed structure as shown in FIG. 1. It encompasses a door 15 to permit entry and exit of the human subject. Attached to the booth are a set of vertical tracks, with servo drive mechanisms and mounting brackets 16 that attach to the circular sensor array to allow the circular sensor array to vertically position the laser range detectors to allow for range measurements for points along the side surfaces of the body subject.

The circular sensor array, shown in FIG. 2, is rigid ring structure with uniformly spaced, fixed mounted, laser range sensors 20. The digital output of each sensor is feed through a set of individually connected wires comprising the power and sensor data bus 12. The rigid ring is attached to three (3) vertical tracks by mounting brackets points 22.

Sensor measurements from the data bus are feed to the SCPU shown in FIG. 4. Mathematical algorithms working inside the processor convert sensor measurements into x, y, z spatial body surface coordinates. The processor then translates those coordinates into a specially defined machine-readable file format for digital storage or transmission.

The digital file can be converted by the magnetic media maker, FIG. 5, and written to any standard digital storage media.

OPERATION—MAIN EMBODIMENT (FIGS. 1 though 5)

The BSDM operates to capture three (3) dimensional coordinates (x, y, z) on the surface of a human or other body placed inside its booth as shown in FIG. 1. Once inside the booth, the top, bottom, and side surfaces of the body are scanned by laser range finders to identify spatial coordinates along the surface of the body. These points are determined from the pre-scan knowledge of the position and pointing of each detector and the range sample made by the laser range finder. The range measurement indicates the distance from the sensor's known position to the body.

The laser range finder, FIG. 3, operates by pointing a highly focused beam of laser light at the body subject for range detection. The frequency of the light source is known by the laser detection mechanism that is tuned to filter and receive the electromagnetic emanations of the source. To determine range using such a device, the laser source is pointed at the subject area to be measured. Laser energy impinging upon the body subject is reflected back into the laser detector. When an impulse is transmitted by the light source, a range measurement is derived from the delay between the impulse transmit and receive times. The associated range measurement constitutes the distance between the body subject and the collocated source-detector unit.

The laser range finders mounted to the top and bottom and on the movable circular ring of the BSDM booth are pointed inward toward the enclosed body subject. The ringed sensor array is moved vertically along the ring tracks to allow for range detection of surface points on the all sides along the body. The top and bottom sensors may be fixed or mechanically repositioned to detect top and bottom surface points.

To protect against co-site interference (i.e., range detection errors arising from energy emanations from other laser range finders), the SCPU times and sequences the energizing of laser sources and sampling of detection mechanisms so that no two sensors tuned to the same laser frequency will be detecting simultaneously. Further, to eliminate range detection errors resulting from laser energy scatter, the entire inside of the body scanner booth is lined with an electromagnetic energy absorptive material.

To protect against possible human eye damage, human subjects will wear an energy reflective eye protection goggle.

The SCPU provides a variety of control and procession functionality as shown in FIG. 4. The Sensor Controller module controls the positioning of sensors and the on/off triggering of sensors for range detection. These control signals are transmitted onto the data bus for distribution to individual sensors as well as the mechanical scan motion control mechanisms. The Sensor Processor module accepts sensor range detection data as input from the data bus. Being logically linked to the Sensor Controller that has sensor spatial and detection calibration knowledge, the Sensor Processor translates range detection data into X, Y, and Z spatial coordinates. The Body Contour Mapper module translates these coordinates into a standard 3-D computer aided design (CAD) model of the body for 3-D analysis. The Body Analyzer module converts the 3-D body model into important, frequently used body measurements such as limb dimensions, typical garment industry measurements, and body volume. The File Formatter module takes all generated data and produces a uniquely formatted BSDM machine-readable ASCII file for storage on digital media or digital transmission to other computing devices.

The Media Production Unit (MPU), shown in FIG. 5, accepts the BSDM file format and writes it to any standard digital media for storage purposes.

DESCRIPTION AND OPERATION—ALTERNATIVE EMBODIMENT

Alternatively to the use of arrays of laser range detectors, it is reasoned that an array of spatially distributed but positionally known charged couple device (CCD) cameras could also be used. Such devices would be used in lieu of laser range detectors and sophisticated image processing software could theoretically be used to identify x, y, and z coordinate points the surface of a body. This embodiment should yield a more rapid body scan time but the resolution of sample points will be dependent upon the sophistication of the image processing software.

CONCLUSION, RAMIFICATIONS, AND SCOPE

In summation, this invention provides a methodology and apparatus for automatically measuring the 3-D surface contours of a human body. It provides a means for generating garment and medical industry body measurements and specifies a system for processing and generating a digital file, containing the spatial coordinates of points along the surface of a measured body, for the purposes of digital storage, transmission, and computer processing.

The BSDM includes a booth for enclosing a human subject, a booth structure for positioning laser range detectors, mechanisms for moving these sensors to measure the entire human body, and processing systems needed to control sensor movement, make body spatial dimension measurements, and output its data and important measurements as a digital file for storage, transmission, and computer processing.

Its application to the garments and retail clothing industry is significant. Essentially, a person can walk into the BSDM booth and have their body measured automatically in a short period of time. The person can then obtain a digital file of their body dimensions. This digital file can then be used by the person for transmission to the local tailor or garment retailer of their choice. It will eliminate the need for manual measurements and could reduce the need for people to try on cloths in fitting rooms.

Using a portable magnetic storage device (e.g., magnetic strip), people could carry their digital body map around while they went shopping and examine the fit of a variety of garments via a store provided computer. The time people spend in a dressing room trying on cloths to understand the way they fit, could be significantly reduced.

For Internet applications, the concept of the Virtual Dressing Room (VDR) will be greatly enhanced since the BSDM will allow people to shop online more effectively. With a digital representation of their body, Internet applications could be designed to allow a person to try on a variety of garments and visualize their fit, while online. This would assist the online garment buyer in the purchase decision and thereby, reduce the return rate associated with poorly fitting garments that are purchased online. Before such e-commerce methods could be adopted by clothing retailers, garment industry standards would need to be developed to support the accurate fitting of garments to full-body dimension maps. Today's garment fitting standards involve a simple set of measures that require a person to actually try on a garment to really understand its fit. This revised set of clothing measurement standards would support online fitting.

For the medical industry, volumetric measurements of the whole body are important for things like fat content and body density analysis. The BSDM provides a simple-to-use, accurate system for performing such analyses.

Accordingly, the scope of this invention should be determined not by the embodiment(s) illustrated, but by the appended claims and their legal equivalents.

We claim:

1. A machine for measuring spatial coordinates of points along the surface contours of a three-dimensional object comprising: an enclosure within which said object is placed, a plurality of laser range finders for detecting the sensor-to-object distance at a multitude of points along the three-dimensional surface contours of said object, said laser range finders operating by emitting and receiving an impulse of radiation with the range measurement being derived from the delay between the impulse transmit and receive times, means for positioning said laser range finders within said enclosure so as to be pointed inwardly toward the object in the enclosure, said range finders being mounted on the top and bottom of the enclosure and being mounted on a structure which is mounted to be movable vertically, with said range finders providing for range detection of surface points on the all sides of the body, and means for generating a digital tabulation of all measured spatial coordinates.

* * * * *